(12) United States Patent
Colman et al.

(10) Patent No.: US 6,284,726 B1
(45) Date of Patent: Sep. 4, 2001

(54) INHIBITION OF ANGIOGENESIS BY PEPTIDE ANALOGS OF HIGH MOLECULAR WEIGHT KININOGEN DOMAIN 5

(75) Inventors: Robert W. Colman, Media; Shaker A. Mousa, New London, both of PA (US)

(73) Assignees: Temple University - Of The Commonwealth System of Higher Education, Philadelphia, PA (US); Du Pont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/612,126

(22) Filed: Jul. 7, 2000

Related U.S. Application Data (63) Continuation of application No. PCT/US99/26377, filed on Nov. 9, 1999.
(60) Provisional application No. 60/107,844, filed on Nov. 10, 1998.

(51) Int. Cl.$^7$ .......................... A61K 38/00; A61K 38/04
(52) U.S. Cl. ................................. 514/2; 514/2; 514/12; 514/16; 435/6; 435/69.8; 435/69.1; 435/91.5; 604/890.1
(58) Field of Search .................. 435/6, 69.8, 69.1, 435/91.5, 320.1; 514/2, 12, 16; 604/890.1

(56) References Cited

U.S. PATENT DOCUMENTS

| | | |
|---|---|---|
| 5,596,079 | 1/1997 | Smith et al. .................... 530/328 |
| 5,756,291 | 5/1998 | Griffin et al. ...................... 435/6 |
| 5,786,365 | 7/1998 | Heitsch et al. ................... 514/311 |
| 5,800,385 * | 9/1998 | Demopulos et al. ............. 604/890.1 |
| 5,817,748 | 10/1998 | Miller et al. ..................... 530/300 |
| 5,830,671 | 11/1998 | Dennis et al. ..................... 435/7.8 |
| 5,846,720 * | 12/1998 | Foulkes et al. ...................... 435/6 |
| 5,846,821 | 12/1998 | Guerinot et al. ................. 435/320.1 |

FOREIGN PATENT DOCUMENTS

| | | |
|---|---|---|
| 782172 | 3/1995 | (JP) . |
| 8208692 | 8/1996 | (JP) . |
| WO 96/41640 | 12/1996 | (WO) . |

OTHER PUBLICATIONS

Auerswald et al., "Cloning, expression, and characterization of human kininogen domain 3", FEBS Letters vol. 321, No. 1, pp. 93–97, 1993.*
Lottspeich et al., "The Amino Acid Sequence of the Light Chain of Human Hign–Molecular–Mass Kininogen", European Journal of Biochemistry, 1985, vol. 152, pp. 307–314.
Takagaki et al., Cloning and Sequence Analysis of cDNAs for Human High Molecular Weight and Low Molecular Weight Prekininogens, The Journal of Biological Chemistry, Jul. 15, 1985, vol. 260, No. 14, pp. 8601–8609.
Kitamura et al., "Structural Organization of Human Kininogen Gene and a Model for its Evolution", The Journal of Biological Chemistry, Jul. 15, 1985, vol. 260, No. 15, pp. 8610–8617.

Colman et al., Contact System: A Vascular Biology Modulator With Anticoagulant, Profibrinolytic, Antiadhesive, and proinflammatory Attributes. Blood, 90(10):3819–3843 (Nov. 15, 1997).
R.W. Colman, et al., Abstract #701, "Inhibition Of Angkiogenesis By Peptides Derived From Kininogen", Blood vol. 92, No. 10 Supplement 1, Nov. 15, 1998.
Heiko Herwald, et al., "Identification of an Endothelial Cell Binding Site on Kininogen Domain D3*", The Journal of Biological Chemistry, vol. 270, No. 24 pp. 14634–14641 (Jun. 16, 1995).
Satya P. Kunapuli et al., "Deletion Mutagenesis of High Molecular Weight Kininogen Light Chain", The Journal of Biological Chemistry vol. 268, No. 4, pp. 2486–2492 (Feb. 5, 1993).
Ahmed A.K. Hasan, et al., "Mapping the Cell Binding Site on High Molecular Weight Kininogen Domain 5*", The Journal of Biological Chemistry, vo. 270, No. 33 pp. 19256–19261 (Aug. 18, 1995).
Robert W. Colman, et al., "Binding of High Molecular Weight Kininogen to Human Endothelial Cells Is Mediated via a Site within domains 2 and 3 of the Urokinase Receptor", J. Clin. Invest., vol. 100, No. 6, pp. 1481–1487 (Sep. 1997).
A.K. Hasan, et al., "The Carboxyl Terminus of Bradykinin and Amino Terminus of the Light Chain of Kininogens comprise an Endothelial Cell Binding Domain", Ahmed The Jorunal of Biological Chemistry, vo. 269, No. 50, pp. 31822–31830 (Dec. 16, 1994).
Mohammad M.H. Khan et al., "Three noncintiguous peptides comprise binding sites on high–molecular–weight kininogen to neutrophils", The American Physiological Society (Heart Circ. Physiol. 44): H145–150, vol. 275 (1998).
Yanina T. Wachtfogel et al., "High Molecular Weight Kininogen Binds to Mac–1 on Neutrophils by Its Heavy Chain (Domain 3) and Its Light Chain (Domain 5)", The Journal of Biological Chemistry, vol. 269, No. 30, pp. 19307–19312 (Jul. 29, 1994).
Shinji Asakura et al., "Inhibition of Cell Adhesion by High Molecular Weight Kininogen", The Journal of Cell Biology, vol. 116, No. 2, pp. 465–476 (Jan. 1992).

* cited by examiner

Primary Examiner—Karen Cochrane Carlson
Assistant Examiner—Patricia Robinson
(74) Attorney, Agent, or Firm—Drinker Biddle & Reath LLP (57) ABSTRACT

Peptide analogs of the high molecular weight kininogen domain 5 are potent inhibitors of angiogenesis. The peptides have the formula $$X_1\text{-(HGLGHGHEQQHGKGH)-}X_2 \qquad (I)$$

wherein $X_1$ is from zero to 25 amino acids;

$X_2$ is from zero to 60 amino acids.

Methods of inhibiting endothelial cell proliferation and angiogenesis are provided.

25 Claims, 1 Drawing Sheet

SEQUENCE LISTING

```
<160> NUMBER OF SEQ ID NOS: 12

<210> SEQ ID NO 1
<211> LENGTH: 255
<212> TYPE: PRT
<213> ORGANISM: Human

<400> SEQUENCE: 1
```

Ser Ser Arg Ile Gly Glu Ile Lys Glu Thr Thr Val Ser Pro Pro
 1               5                  10                  15

His Thr Ser Met Ala Pro Ala Gln Asp Glu Arg Asp Ser Gly Lys
            20                  25                  30

Glu Gln Gly His Thr Arg Arg His Asp Trp Gly His Glu Lys Gln Arg
         35                  40                  45

Lys His Asn Leu Gly His Gly His Lys His Glu Arg Asp Gln Gly His
     50                  55                  60

Gly His Gln Arg Gly His Gly Leu Gly His Gly His Glu Gln Gln His
 65                  70                  75                  80

Gly Leu Gly His Gly His Lys Phe Lys Leu Asp Asp Leu Glu His
                 85                  90                  95

Gln Gly Gly His Val Leu Asp His Gly Lys His Lys His Gly His
                100                 105                 110

Gly His Gly Lys His Lys Asn Lys Gly Lys Lys Asn Gly Lys His Asn
                115                 120                 125

Gly Trp Lys Thr Glu His Leu Ala Ser Ser Glu Asp Ser Thr Thr
            130                 135                 140

Pro Ser Ala Gln Thr Gln Glu Lys Thr Glu Gly Pro Thr Pro Ile Pro
145                 150                 155                 160

Ser Leu Ala Lys Pro Gly Val Thr Val Thr Phe Ser Asp Phe Gln Asp
                165                 170                 175

Ser Asp Leu Ile Ala Thr Met Met Pro Pro Ile Ser Pro Ala Pro Ile
                180                 185                 190

Gln Ser Asp Asp Asp Trp Ile Pro Asp Ile Gln Thr Asp Pro Asn Gly
            195                 200                 205

Leu Ser Phe Asn Pro Ile Ser Asp Phe Pro Asp Thr Thr Ser Pro Lys
    210                 215                 220

Cys Pro Gly Arg Pro Trp Lys Ser Val Ser Glu Ile Asn Pro Thr Thr
225                 230                 235                 240

Gln Met Lys Glu Ser Tyr Tyr Phe Asp Leu Thr Asp Gly Leu Ser
                245                 250                 255

```
<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      His (441) through His (455)

<400> SEQUENCE: 2
```

His Gly Leu Gly His Gly His Glu Gln Gln His Gly Leu Gly His
 1               5                  10                  15

```
<210> SEQ ID NO 3
<211> LENGTH: 21
<212> TYPE: PRT
```

```
<213> ORGANISM: Artificial Sequence
<220> FEATURE:
<223> OTHER INFORMATION: Description of Artificial Sequence: Human high
      molecular weight kininogen light chain amino acids
      Lys(420) through Gly(440)

<400> SEQUENCE: 3

Lys His Asn Leu Gly His Gly His Lys His Glu Arg Asp Gln Gly His
 1               5                  10                  15

Gly His Gln Arg Gly
            20

<210> SEQ ID NO 4
<211> LENGTH: 47
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      Gly(456) through Lys(502)

<400> SEQUENCE: 4

Gly His Lys Phe Lys Leu Asp Asp Asp Leu Glu His Gln Gly Gly His
 1               5                  10                  15

Val Leu Asp His Gly His Lys His Lys His Gly His Gly His Gly Lys
            20                  25                  30

His Lys Asn Lys Gly Lys Lys Asn Gly Lys His Asn Gly Trp Lys
        35                  40                  45

<210> SEQ ID NO 5
<211> LENGTH: 55
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      Lys(420) through Asp(474)

<400> SEQUENCE: 5

Lys His Asn Leu Gly His Gly His Lys His Glu Arg Asp Gln Gly His
 1               5                  10                  15

Gly His Gln Arg Gly His Gly Leu Gly His Gly His Glu Gln Gln His
            20                  25                  30

Gly Leu Gly His Gly His Lys Phe Lys Leu Asp Asp Asp Leu Glu His
        35                  40                  45

Gln Gly Gly His Val Leu Asp
    50                  55

<210> SEQ ID NO 6
<211> LENGTH: 83
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      Lys(420) through Lys(502)

<400> SEQUENCE: 6

Lys His Asn Leu Gly His Gly His Lys His Glu Arg Asp Gln Gly His
 1               5                  10                  15

Gly His Gln Arg Gly His Gly Leu Gly His Gly His Glu Gln Gln His
            20                  25                  30

Gly Leu Gly His Gly His Lys Phe Lys Leu Asp Asp Asp Leu Glu His
        35                  40                  45
```

```
Gln Gly Gly His Val Leu Asp His Gly His Lys His Lys His Gly His
         50                  55                  60

Gly His Gly Lys His Lys Asn Lys Gly Lys Lys Asn Gly Lys His Asn
 65                  70                  75                  80

Gly Trp Lys

<210> SEQ ID NO 7
<211> LENGTH: 62
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      His(441) through Lys(502)

<400> SEQUENCE: 7

His Gly Leu Gly His Gly His Glu Gln Gln His Gly Leu Gly His Gly
 1               5                  10                  15

His Lys Phe Lys Leu Asp Asp Asp Leu Glu His Gln Gly Gly His Val
                 20                  25                  30

Leu Asp His Gly His Lys His Lys His Gly His Gly His Gly Lys His
             35                  40                  45

Lys Asn Lys Gly Lys Lys Asn Gly Lys His Asn Gly Trp Lys
 50                  55                  60

<210> SEQ ID NO 8
<211> LENGTH: 186
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      His(441) through Ser(626)

<400> SEQUENCE: 8

His Gly Leu Gly His Gly His Glu Gln Gln His Gly Leu Gly His Gly
 1               5                  10                  15

His Lys Phe Lys Leu Asp Asp Asp Leu Glu His Gln Gly Gly His Val
                 20                  25                  30

Leu Asp His Gly His Lys His Lys His Gly His Gly His Gly Lys His
             35                  40                  45

Lys Asn Lys Gly Lys Lys Asn Gly Lys His Asn Gly Trp Lys Thr Glu
 50                  55                  60

His Leu Ala Ser Ser Ser Glu Asp Ser Thr Thr Pro Ser Ala Gln Thr
 65                  70                  75                  80

Gln Glu Lys Thr Glu Gly Pro Thr Pro Ile Pro Ser Leu Ala Lys Pro
                 85                  90                  95

Gly Val Thr Val Thr Phe Ser Asp Phe Gln Asp Ser Asp Leu Ile Ala
                100                 105                 110

Thr Met Met Pro Pro Ile Ser Pro Ala Pro Ile Gln Ser Asp Asp Asp
            115                 120                 125

Trp Ile Pro Asp Ile Gln Thr Asp Pro Asn Gly Leu Ser Phe Asn Pro
        130                 135                 140

Ile Ser Asp Phe Pro Asp Thr Thr Ser Pro Lys Cys Pro Gly Arg Pro
145                 150                 155                 160

Trp Lys Ser Val Ser Glu Ile Asn Pro Thr Thr Gln Met Lys Glu Ser
                165                 170                 175

Tyr Tyr Phe Asp Leu Thr Asp Gly Leu Ser
```

180                185

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      Gly(440) through His(455)

<400> SEQUENCE: 9

Gly His Gly Leu Gly His Gly His Glu Gln Gln His Gly Leu Gly His
 1               5                  10                  15

<210> SEQ ID NO 10
<211> LENGTH: 94
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      Lys(420) through Ser(513)

<400> SEQUENCE: 10

Lys His Asn Leu Gly His Gly His Lys His Glu Arg Asp Gln Gly His
 1               5                  10                  15

Gly His Gln Arg Gly His Gly Leu Gly His Gly His Glu Gln Gln His
                20                  25                  30

Gly Leu Gly His Gly His Lys Phe Lys Leu Asp Asp Asp Leu Glu His
                35                  40                  45

Gln Gly Gly His Val Leu Asp His Gly His Lys His Lys His Gly His
         50                  55                  60

Gly His Gly Lys His Lys Asn Lys Gly Lys Lys Asn Gly Lys His Asn
 65                  70                  75                  80

Gly Trp Lys Thr Glu His Leu Ala Ser Ser Ser Glu Asp Ser
                 85                  90

<210> SEQ ID NO 11
<211> LENGTH: 179
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      Glu(448) through Ser(626)

<400> SEQUENCE: 11

Glu Gln Gln His Gly Leu Gly His Gly His Lys Phe Lys Leu Asp Asp
 1               5                  10                  15

Asp Leu Glu His Gln Gly Gly His Val Leu Asp His Gly His Lys His
                20                  25                  30

Lys His Gly His Gly His Gly Lys His Lys Asn Lys Gly Lys Lys Asn
         35                  40                  45

Gly Lys His Asn Gly Trp Lys Thr Glu His Leu Ala Ser Ser Ser Glu
     50                  55                  60

Asp Ser Thr Thr Pro Ser Ala Gln Thr Gln Glu Lys Thr Glu Gly Pro
 65                  70                  75                  80

Thr Pro Ile Pro Ser Leu Ala Lys Pro Gly Val Thr Val Thr Phe Ser
                 85                  90                  95

Asp Phe Gln Asp Ser Asp Leu Ile Ala Thr Met Met Pro Pro Ile Ser

-continued

```
                        100                 105                 110
Pro Ala Pro Ile Gln Ser Asp Asp Trp Ile Pro Asp Ile Gln Thr
        115                 120                 125
Asp Pro Asn Gly Leu Ser Phe Asn Pro Ile Ser Asp Phe Pro Asp Thr
        130                 135                 140
Thr Ser Pro Lys Cys Pro Gly Arg Pro Trp Lys Ser Val Ser Glu Ile
145                 150                 155                 160
Asn Pro Thr Thr Gln Met Lys Glu Ser Tyr Tyr Phe Asp Leu Thr Asp
                165                 170                 175
Gly Leu Ser

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Human high
      molecular weight kininogen light chain amino acids
      His(475) through His(485)

<400> SEQUENCE: 12

His Gly His Lys His Lys His Gly His Gly His
 1               5                  10
```

INHIBITION OF ANGIOGENESIS BY PEPTIDE ANALOGS OF HIGH MOLECULAR WEIGHT KININOGEN DOMAIN 5

CROSS-REFERENCE TO RELATED APPLICATION

This Appln is a con't of PCT/US99/26377 filed Nov. 9, 1999 which claim the benefit of U.S. provisional patent application Ser. No. 60/107,844, filed Nov. 10, 1998, is hereby claimed. The entire disclosure of the aforesaid provisional patent application is incorporated herein by reference.

FIELD OF THE INVENTION

The invention relates to therapeutic compounds and methods for inhibiting angiogenesis.

BACKGROUND OF THE INVENTION

Angiogenesis

Angiogenesis is the process in which new blood vessels grow into an area which lacks a sufficient blood supply. Angiogenesis commences with the erosion of the basement membrane surrounding endothelial cells and pericytes forming capillary blood vessels. Erosion of the basement membrane is triggered by enzymes released by endothelial cells and leukocytes. The endothelial cells then migrate through the eroded basement membrane when induced by angiogenic stimulants. The migrating cells form a "sprout" off the parent blood vessel. The migrating endothelial cells proliferate, and the sprouts merge to form capillary loops, thus forming a new blood vessel.

Angiogenesis can occur under certain normal conditions in mammals such as in wound healing, in fetal and embryonic development, and in the formation of the corpus luteum, endometrium and placenta. Angiogenesis also occurs in certain disease states such as in tumor formation and expansion, or in the retina of patients with certain ocular disorders. Angiogenesis can also occur in a rheumatoid joint, hastening joint destruction by allowing an influx of leukocytes with subsequent release of inflammatory mediators.

The evidence for the role of angiogenesis in tumor growth was extensively reviewed and present by O'Reilly and Folkman in U.S. Pat. No. 5,639,725, the entire disclosure of which is incorporated herein by reference. It is now generally accepted that the growth of tumors is critically dependent upon this process.

High Molecular Weight Kininogen

High molecular weight kininogen (HK) is a 120 kD glycoprotein containing heavy and light chains, composed of domains 1 through 3, and 5 and 6, respectively. This form of HK is often referred to as "single-chain high molecular weight kininogen". HK binds with high affinity to endothelial cells, where it is cleaved by plasma kallikrein into heavy and light chains. This form of cleaved HK is known as "two-chain high molecular weight kininogen" ($HK_a$). The heavy and light chains are linked by domain 4 in intact HK; domain 4 contains bradykinin, a potent biologically active nonapeptide. Bradykinin is released from HK through cleavage mediated by plasma kallikrein (Kaplan et al., *Blood* 70:1–15, 1987). The heavy and light chains resulting from the elimination of bradykinin remain linked by a disulfide bond between cysteine residues at positions 10 and 596. Conversion of HK to $HK_a$ is accompanied by a dramatic structural rearrangement. The central globular region of HK is separated after bradykinin liberation and rearranged with cysteine protease inhibitory regions opposite the prekal-likrein binding region (Weisel et al., *J. Biol. Chem.* 262:1405, 1987).

The HK light chain consists of the following sequence of HK amino acids 372–626 (SEQ ID NO:1):

SSRIGEIKEETTVSPPHTSMAPAQDEERD SGKEQGHTRRHD-
WGHEKQRKHNLGHGH KHERDQGHGHQRGHGLGH-
GHEQQHGLG HGHKFKLDDDLEHQGGHVLDHGHKHKH
GHGHGKHKNKGKKNGKHNGWKTEHLAS SSEDSTTP-
SAQTQEKTEGPTPIPSLAKPG VTVTFSDFQDSDLIATMMP-
PISPAPIQSD DDWIPDIQTDPNGLSFNPISDFPDTTSPK
CPGRPWKSVSEINPTTQMKESYYFDLTD
GLS                                                      (SEQ ID NO:1).

The HK light chain consists of HK amino acids serine-372 to threonine 383, forming the C-terminal portion of HK domain 4 remaining after bradykinin liberation; HK amino acids valine 384 to lysine 502, forming the HK domain 5 (D5); and HK amino acids threonine 503 to serine 626, forming the HK domain 6 (D6). D5 is rich in histidines, glycines and lysines and has been postulated to be involved in binding to negatively charged surfaces. D5 serves as a cell binding site on platelets, granulocytes and endothelial cells. For a recent review including a discussion of HK's domain structure, and the functional significance of the various domains (including D5), see Colman and Schmaier, *Blood* 90:3819–3843 (1997). $HK_a$ has been shown to bind to the urokinase receptor (uPAR) on endothelial cells (Colman et al., *J. Clin. Invest.* 100:1481–7 (1997). HK D5 has been shown to participate in cell binding; certain peptides from regions of D5 have been found to inhibit HK binding to endothelial cells (Hasan et al., *J. Biol. Chem.*, 270:19256, 1995). Despite these findings, no role has been suggested for HK in the process of angiogenesis.

SUMMARY OF THE INVENTION

The compounds of the present invention are in the form of peptides which possess anti-angiogenic activity.

In all embodiments, the peptide may optionally comprise an amino-terminal and/or carboxy-terminal protecting group.

Compounds possessing anti-angiogenic activity are derived from HK domain 5 and 6 have the formula $$X_1\text{-(SEQ ID NO:2)-}X_2 \quad (I)$$

wherein
$X_1$ is from zero to 25 amino acids;
$X_2$ is from zero to 60 amino acids; and
SEQ ID NO:2 is the amino acid sequence corresponding to HK light chain His(441)-His(455): HGLGHGHEQQ HGLGH.

According to one embodiment of the invention, $X_1$ is from zero to 12 amino acids, more preferably from zero to 6 amino acids; and $X_2$ is from zero to 45 amino acids, more preferably from zero to 32 amino acids, more preferably from zero to 22 amino acids, most preferably from zero to six amino acids.

In certain preferred compounds,
$X_1$ is
  (i) zero amino acids, or
  (ii) the segment KHNLGHGHKHE RDQGHGHQRG (SEQ ID NO:3), or N-terminal truncation fragment thereof containing at least one amino acid, and
$X_2$ is
  (i) zero amino acids, or
  (ii) the segment GHKFKLDDDDLEHQG GHVLDH-GHKHKHGHGHGKHKNKGK KNGKHNGWK (SEQ ID NO:4), or C-terminal truncation fragment thereof containing at least one amino acid.

SEQ ID NO:3 and NO:4 correspond to HK light chain amino acids Lys(420)-Gly(440) and Gly(456)-Lys(502), respectively.

According to a further preferred embodiment of the invention, $X_1$ has a substantial amino acid homology to SEQ ID NO:3 and $X_2$ has a substantial amino acid homology to SEQ ID NO:4.

Exemplary and preferred compounds of formula I include:

(a) GHGLGHGHEQQHGLGH (SEQ ID NO:9), corresponding to HK light chain amino acids Gly(440)-His(455);

(b) KHNLGHGHKHERDQGHGHQRG HGLGH-GHEQQHGLGHGHKFKL DDDLEHQGGHVLD (SEQ ID NO:5), corresponding to HK light chain amino acids Lys(420)-Asp(474);

(c) KHNLGHGHKHERDQGHGHQRG HGLGH-GHEQQHGLGHGHKFKL DDDLEHQGGHVLDH-GHKHKHG HGHGKHKNKGKKNGKHNGWK (SEQ ID NO:6), corresponding to HK light chain amino acids Lys(420)-Lys(502);

(d) HGLGHGHEQQHGLGHGHKFKL DDDLEHQG-GHVLDHGHKHKHG HGHGKHKNKGKKNGKH-NGWK (SEQ ID NO:7), corresponding to HK light chain amino acids His(441)-Lys(502); and (e) KHNLGHGHKHERDQGHGHQRG HGLGH-GHEQQHGLGHGHKFKL DDDLEHQGGHVLDHGH-KHKHG HGHGKHKNKGKKNGKHNGWKT EHLASSSEDS (SEQ ID NO:10), corresponding to HK light chain amino acids Lys(420)-Ser(513).

According to a related aspect of the invention, the anti-angiogenic compound has the amino acid sequence of HK light chain amino acids His(475)-His(485), that is, SEQ ID NO:11: HGHKHKHG HGH.

According to another related aspect of the invention, the anti-angiogenic compound has the amino acid sequence of HK light chain amino acids His(441)-Ser(626), that is, SEQ ID NO:8:

> HGLGHGHEQQHGLGHGHKFKL DDDLEHQGGHVLDHGH-
> KHKHG HGHGKHKNKGKKNGKHNGWKT EHLASSSED-
> STTPSAQTQEKTE GPTPIPSLAKPGVTVTFSDFQD SDLI-
> ATMMPPISPAPIQSDDDW IPDIQTDPNGLSFNPISDFPDTT
> SPKCPGRPWKSVSEINPTTQMK ESYYFD
> LTDGLS (SEQ ID NO:8).

According to another related aspect of the invention, the anti-angiogenic compound has the amino acid sequence of HK light chain amino acids Glu(448)-Ser(626), that is, SEQ ID NO:12:

> EQQHGLGHGHKFKLDDDLEHQ GGHVLDHGHKHKHGHGH-
> GKHK NKGKKNGKHNGWKTEHLASSS EDSTTP-
> SAQTQEKTEGPTPIPS LAKPGVTVTFSDFQDSDLIATM
> MPPISPAPIQSDDDWIPDIQTDP NGLSFNPISDFPDTTSP-
> KCPGR PWKSVSEINPTTQMKESYYFDL
> TDGLS (SEQ ID NO:12).

SEQ ID NOS:8 and 12 begin in domain 5 and extend through the entirety of domain 6.

The invention also encompasses a method of inhibiting endothelial cell proliferation comprising contacting endothelial cells with a compound of formula I, or with the compound of SEQ ID NO:8, 11 or 12.

The invention also encompasses a method of inhibiting migration of endothelial cells to vitronectin comprising contacting endothelial cells with a compound of formula I, or with the compound of SEQ ID NO:8, 11 or 12.

The invention is also a composition comprising a pharmaceutically effective carrier and a compound of formula I, or the compound of SEQ ID NO:8, 11 or 12.

The invention is also a method of inhibiting angiogenesis in a mammal in need of such treatment comprising administering to said mammal a therapeutically effective amount of a composition comprising a pharmaceutically effective carrier and a compound of formula I, or with the compound of SEQ ID NO:8, 11 or 12. The mammal treated is preferably a human being.

Other aspects and advantages of the present invention are described in the following detailed description of the preferred embodiments thereof.

Abbreviations and Short Forms

The following abbreviations and short forms are used in this specification.

"bFGF" is recombinant human basic fibroblast growth factor

"GST" means glutathione-S-transferase.

"HK" means the mature form of high molecular weight kininogen, and any allelic variations thereof. By "mature" is meant the post-translationally-modified form of HK which results from cleavage of an eighteen amino acid leader from the initially translated molecule. All numbering with respect to amino acid positions of HK is from the N-terminus of the mature form as position 1. "HK" is synonymous with "single chain HK", that is, the mature form of high molecular weight kininogen prior to cleavage by kallikrein and the formation of two-chain high molecular weight kininogen.

"$HK_a$" means two-chain high molecular weight kininogen, the product of kallikrein cleavage of mature high molecular weight kininogen, and any allelic variations thereof.

"HUVEC" means human umbilical vein endothelial cell

"VEGF" means vascular endothelial cell growth factor.

Amino Acid Abbreviations

The nomenclature used to describe polypeptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| A | Alanine | Ala |
|---|---------|-----|
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |
| T | Threonine | Thr |
| V | Valine | Val |
| W | Tryptophan | Trp |
| Y | Tyrosine | Tyr |

Definitions

The following definitions, of terms used throughout the specification, are intended as an aid to understanding the scope and practice of the present invention.

"Angiogenesis" means the generation of new blood vessels into a tissue or organ.

A "peptide" is a compound comprised of amino acid residues covalently linked by peptide bonds.

The expression "amino acid" as used herein is meant to include both natural and synthetic amino acids, and both D and L amino acids. "Natural amino acid" means any of the twenty primary, naturally occurring amino acids which typically form peptides, polypeptides, and proteins. "Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity. Additionally, a disulfide linkage may be present or absent in the peptides of the invention, as long as anti-angiogenic activity is maintained.

Amino acids have the following general structure:

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. Peptides comprising a large number of amino acids are sometimes called "polypeptides". The amino acids of the peptides described herein and in the appended claims are understood to be either D or L amino acids, or mixtures thereof, with L amino acids being preferred.

"Homology" means similarity of sequence reflecting a common evolutionary origin. Peptides or proteins are said to have homology, or similarity, if a substantial number of their amino acids are either (1) identical, or (2) have a chemically similar R side chain. Nucleic acids are said to have homology if a substantial number of their nucleotides are identical.

As used herein, "protected" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides,* vol. 3, pp. 3–88 (Academic Press, New York, 1981) for suitable protecting groups.

As used herein, "protected" with respect to a terminal carboxyl group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

"Substantial amino acid sequence homology" means an amino acid sequence homology greater than about 30%, preferably greater than about 60%, more preferably greater than about 80%, and most preferably greater than about 90%.

By "N-terminal truncation fragment" with respect to an amino acid sequence is meant a fragment obtained from a parent sequence by removing one or more amino acids from the N-terminus thereof.

By "C-terminal truncation fragment" with respect to an amino acid sequence is meant a fragment obtained from a parent sequence by removing one or more amino acids from the C-terminus thereof.

BRIEF DESCRIPTION OF THE FIGURES

FIGS. 1A–1D show the results of a chick chorioallantoic membrane angiogenesis assay. Embryonated chicken eggs were treated with saline (FIG. 1A), recombinant human basic fibroblast growth factor (bFGF) (FIG. 1B), bFGF plus glutathione-S-transferase (GST) (FIG. 1C), or bFGF plus the GST fusion peptide GST-SEQ ID NO:10 (FIG. 1D). The substantial inhibition of bFGF-induced angiogenesis by GST-SEQ ID NO:10 is apparent in FIG. 1D.

DETAILED DESCRIPTION OF THE INVENTION

The present invention is based upon the discovery that peptide analogs of HK domain 5 inhibit endothelial cell proliferation. This activity confers upon the domain 5 peptides the ability to inhibit cytokine-driven angiogenesis in vivo. According to the assays utilized herein, the peptides potently inhibit the proliferation of human endothelial cells in vitro in response to a typical endothelial cell growth factor, bFGF.

Endothelial cells must migrate prior to penetrating the basement membrane. Migration of endothelial cells to vitronectin is a process closely related to angiogenesis. The peptides of the invention inhibit migration of endothelial cells to vitronectin.

Furthermore, as shown herein, the peptides of the invention are effective in an in vivo model of angiogenesis. The peptides inhibit the ingrowth of new blood vessels in the chorioallantoic membrane of intact living chicken eggs stimulated with endothelial cell growth factor.

The mature human HK light chain amino acid sequence is set forth herein as SEQ ID NO:1. Structurally, domain 5 comprises amino acids 372 to 502, but the segment 372-419 can be removed without prejudice to the function of the remaining portion. The 372-419 segment may be removed by kallikrein cleavage between Arg(419) and Lys(420). Peptides containing the D5 segment SEQ ID NO:2, and certain other D5 peptides as well, inhibit endothelial cell proliferation and are useful as anti-angiogenic agents.

The D5-derived peptides of the present invention may be recombinant peptides, natural peptides, or synthetic peptides. They may also be chemically synthesized, using, for example, solid phase synthesis methods.

In conventional peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group, various coupling reagents (e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology. The preferred peptide synthesis method follows conventional Merrifield solid-phase procedures. See Merrifield, *J. Amer. Chem. Soc.* 85:2149–54 (1963) and *Science* 50:178–85 (1965). Additional information about the solid phase synthesis procedure can be had by reference to the treatise by Steward and Young (*Solid Phase Peptide Synthesis,* W. H. Freeman & Co., San Francisco, 1969, and the review chapter by Merrifield in *Advances in Enzymology* 32:221–296, F. F. Nold, Ed., Interscience Publishers, New York, 1969; and Erickson and Merrifield, *The Proteins* 2:255 et seq. (ed. Neurath and Hill), Academic Press, New York, 1976. The synthesis of peptides by solution methods is described in Neurath et al., eds. (*The Proteins,* Vol. II, 3d Ed., Academic Press, NY (1976)).

Crude peptides may be purified using preparative high performance liquid chromatography. The amino terminus may be blocked according, for example, to the methods described by Yang et al. (*FEBS Lett.* 272:61–64 (1990)).

Peptide synthesis includes both manual and automated techniques employing commercially available peptide synthesizers. The D5-derived peptides may be prepared by chemical synthesis and biological activity can be tested using the methods disclosed herein.

Alternatively, the D5-derived peptides may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered.

The techniques of recombinant DNA technology are known to those of ordinary skill in the art. General methods for the cloning and expression of recombinant molecules are described in Maniatis (*Molecular Cloning,* Cold Spring Harbor Laboratories, 1982), and in Sambrook (*Molecular Cloning,* Cold Spring Harbor Laboratories, Second Ed., 1989), and in Ausubel (*Current Protocols in Molecular Biology,* Wiley and Sons, 1987), which are incorporated by reference. The complete cDNA of human HK is reported, for example, by Takagi et al., *J. Biol. Chem.* 260:8601–8609 (1985), the entire disclosure of which is incorporated herein by reference. From this nucleic acid sequence, synthetic genes encoding D5-derived peptides may be synthesized directly on a DNA synthesizer, or may be synthesized as complementary oligonucleotides which are ligated together to form the synthetic gene.

The nucleic acids encoding D5-derived peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate to be immunized. Selection of the appropriate regulatory region or regions is a routine matter, within the level of ordinary skill in the art.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lacl, lacZ, T3, T7, lambda Pr' Pl' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

Examples of polyadenylation signals that can be used in the present invention include but are not limited to SV40 polyadenylation signals and LTR polyadenylation signals.

The peptides of the present invention may be prepared as glutathione-S-transferase (GST) fusion proteins according to the procedure of Kunapuli et al., *J. Biol. Chem.* 268:2486–2492 (1993), the entire disclosure of which is incorporated herein by reference. The fusion proteins are generated by deletion mutagenesis using plasmid pSK931, the derivation of which is described by Kanapuli et al. Plasmid pSK931 was generated as described by Kunapuli et al. by engineering of plasmid pHKG6 of Takagaki et al., *J. Biol. Chem.* 260:8601–8690 (1985). Plasmids capable of expressing the desired fragments of HK light chain are constructed by digestion of pSK931 with a combination of restriction enzymes and religating the plasmid with oligonucleotide linkers in order to retain the reading frame. The recombinant proteins are then purified by glutathione-Sepharose affinity chromatography, eluting bound recombinant protein with glutathione. The recombinant proteins contain GST at their N-terminus.

The D5-derived peptides prepared by either chemical synthesis or recombinant DNA technology may then be assayed for biological activity according to the assay methods described herein.

In some embodiments, the peptides of the present invention may be used in the form of a pharmaceutically acceptable salt.

Suitable acids which are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts with the peptides include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The present invention provides methods for inhibiting angiogenesis. A preferred embodiment is a method of inhibiting the proliferation of endothelial cells. Accordingly, one or more D5-derived peptides of the present invention are administered to a patient in need of such treatment. A therapeutically effective amount of the drug may be administered as a composition in combination with a pharmaceutically carrier.

Pharmaceutically acceptable carriers include physiologically tolerable or acceptable diluents, excipients, solvents, adjuvants, or vehicles, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, polyethyleneglycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, agar-agar and tragacanth, or mixtures of these substances, and the like.

The pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

The compositions may be administered by any convenient route which will result in delivery to the site of undesired angiogenesis in an amount effective for inhibiting that angiogenesis from proceeding. Modes of administration include, for example, orally, rectally, parenterally (intravenously, intramuscularly, intraarterially, or subcutaneously), intracisternally, intravaginally, intraperitoneally, locally (powders, ointments or drops), or as a buccal or nasal spray or aerosol. The compositions can also be delivered through a catheter for local delivery at a target site, or via a biodegradable polymer. The compositions may also be complexed to ligands, or antibodies, for targeted delivery of the compositions.

The compositions are most effectively administered parenterally, preferably intravenously or subcutaneously. For intravenous administration, they may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. If the peptides are sufficiently small (e.g., less than about 8–10 amino acids) other preferred routes of administration are intranasal, sublingual, and the like. Intravenous or subcutaneous administration may comprise, for example, injection or infusion.

The compositions according to the invention can be administered in any circumstance in which inhibition of angiogenesis is desired. Disease states which may be treated include but are not limited to cancer, rheumatoid arthritis, and certain ocular disorders characterized by undesired vascularization of the retina. Because the peptides of the invention are anti-angiogenic, cancers characterized by the growth of solid tumors through angiogenesis of the tissue surrounding the tumor site may be treated according to the invention. Other angiogenesis mediated diseases, which may be treated according to the practice of the present invention, include the angiogenesis mediated diseases listed in U.S. Pat. No. 5,733,876 at col. 10, lines 2–19.

The amount of active agent administered depends upon the degree of the anti-angiogenic effect desired. Those skilled in the art will derive appropriate dosages and schedules of administration to suit the specific circumstances and needs of the patient. Typically, dosages are from about 0.1 to about 100, preferably from about 0.5 to about 50, most preferably from about 1 to about 20, mg/kg of body weight. The active agent may be administered by injection daily, over a course of therapy lasting two to three weeks, for example. Alternatively, the agent may be administered by continuous infusion, such as via an implanted subcutaneous pump.

Intravenous or subcutaneous administration is preferred. The active agent may be given by continuous intravenous infusion over a period of 4–5 days, for example. For subcutaneous administration, the agent may be given every 12 hours, for example, with dosage adjustment based upon pharmacokinetic studies.

Peptides which inhibit endothelial cell proliferation by at least 60%, more preferably by at least 90%, most preferably by 100%, when incubated with such cells at a concentration of 0.27 $\mu$M are preferred. Peptides which inhibit endothelial cell proliferation with an $IC_{50}$ of no more than about 0.1 $\mu$M, more preferably no more than about 0.01, are particularly preferred. For purposes of this preference, percent inhibition of proliferation and $IC_{50}$ are determined with regard to the assay method set forth in Example 1, below.

The present invention is illustrated by the following non-limiting examples.

Example 1
Effect of High Molecular Weight Kininogen Peptides on Endothelial Cell Proliferation The following HK light chain peptides were prepared as glutathione-S-transferase (GST) fusion proteins according to the procedure of Kanapuli et al., *J. Biol. Chem.* 268:2486–2492 (1993), the entire disclosure of which is incorporated herein by reference:

| | |
|---|---|
| GST-Lys(420)-Ser(513) | (GST-SEQ ID NO:10) |
| GST-Lys(420)-Asp(474) | (GST-SEQ ID NO:5) |
| GST-His(441)-Ser(626) | (GST-SEQ ID NO:8) |
| GST-Glu(448)-Ser(626) | (GST-SEQ ID NO: 12) |

The following HK domain 5 peptides were chemically synthesized:

| | |
|---|---|
| Gly(440)-His(455) | (SEQ ID NO:9) |
| His(475)-His(485) | (SEQ ID NO:11). |

SEQ ID NOS:5, 9, 10 and 11 are substantially contained within HK domain 5. SEQ ID NOS:8 and 12 begin in domain 5 and extend into domain 6 to the C-terminus of the HK light chain.

The fusion proteins were generated by deletion mutagenesis using plasmid pSK931. Plasmid pSK931 was generated as described by Kunapuli et al. by engineering of plasmid pHKG6 of Takagaki et al., *J. Biol. Chem.* 260:8601–8690 (1985). Plasmids capable of expressing the desired fragments of HK light chain were constructed by digestion of pSK931 with a combination of restriction enzymes and religating the plasmid with oligonucleotide linkers in order to retain the reading frame. The recombinant proteins were then purified by glutathione-Sepharose affinity chromatography, eluting bound recombinant protein with glutathione.

Cell proliferation was determined by using CyQUANT cell proliferation assay kit from Molecular Probes (catalog #C-7026). The basis for the CyQUANT assay is the use of a proprietary green fluorescent dye (CyQUANT GR dye) which exhibits strong fluorescence enhancement when bound to cellular nucleic acids.

HUVEC cells (50,000/well) in a 96 well microtiter plate were stimulated with 10 ng/ml bFGF in serum-free, M199 growth medium with or without HK peptide for 48 hours at 37° C. in a $CO_2$ incubator. Cells were washed with serum-free medium and frozen at −40° C. Frozen cells were thawed and lysed with a lysis buffer containing the CyQUANT GR dye. Fluorescence was measured using a Cytofluor II Fluorescence Multi-well plate reader with excitation 485 nm and emission with 530 nm.

The percent inhibition of proliferation at a specific peptide concentration was determined for some peptides. For other peptides, an $IC_{50}$ was calculated from a curve plotting inhibitor concentration versus percent inhibition over a inhibition range of ten to ninety percent inhibition.

The results are set forth in Table 1.

TABLE 1

| Peptide | Sequence | Peptide Conc. ($\mu$M) | $IC_{50}$ ($\mu$M) | Proliferation % Inhibition |
|---|---|---|---|---|
| GST-SEQ ID NO: 10 | Lys (420)–Ser (513) | 0.27 | <0.03 | 100 |
| GST-SEQ ID NO: 5 | Lys (420)–Asp (474) | 0.36 | — | 94 |
| GST-SEQ ID NO: 8 | His (441)–Ser (626) | 0.39 | — | 100 |
| SEQ ID NO: 9 | Gly (440)–His (455) | — | 0.102 | — |
| SEQ ID NO: 11 | His (475)–His (485) | — | 0.892 | — |
| GST-SEQ ID NO: 12 | Glu (448)–Ser (626) | 0.35 | — | 65 |

These results demonstrate that the formula 1 peptide analogs, and certain other domain 5 analogs, are potent inhibitors of endothelial cell proliferation.

Example 2
In Ovo Chick Chorioallantoic Membrane Angiogenesis Assay

The effect of the HK domain 5 peptides on cytokine-stimulated angiogenesis in vivo was determined as follows, utilizing GST-SEQ ID NO:10.

New vessels, quantified by blood vessel branching, occurred in response to bFGF, VEGF, or a combination of both. Accordingly, ten day old embryonated chicken eggs were candled to illuminate blood vessels under the shell. An area with a minimum of small blood vessel was identified. The chorioallantoic membrane (CAM) was dropped away from the egg shell in this area by grinding a small hole in the mineralized shell and applying pressure to the underlying inner shell membrane. This caused an air pocket to shift from the wide end of the egg to the identified area and forced a circular region of the CAM approximately 2 cm in diameter to drop away from the shell. A window was cut in the egg shell. A cortisone acetate pre-treated filter disc 5 mm in diameter that was saturated in 1 $\mu$g/mi bFGF, a combination of bFGF and VEGF, or saline and was placed on the CAM. The window in the shell was sealed with adhesive tape and the egg was incubated for four days. Peptide GST-SEQ ID NO:10 (0–25 $\mu$g in 25 $\mu$l saline; 0.27 $\mu$M) was applied to the saturated filter 24 hours later and was applied to the stimulated CAM. The CAM was then harvested on the fourth day of stimulation. Data were evaluated in terms of average number of blood vessel branch points per treatment group as well as percent of control using a video camera attached to a personal computer. Under the conditions of the assay, peptide GST-SEQ ID NO:10 inhibited bFGF-stimulated angiogenesis by 97% and bFGF/VEGF-stimulated angiogenesis by 94%. There was no inhibition of bFGF-stimulated angiogenesis by GST alone (<10% inhibition).

Figure 1A:
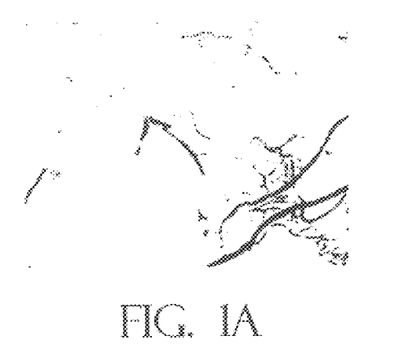
Figure 1B:
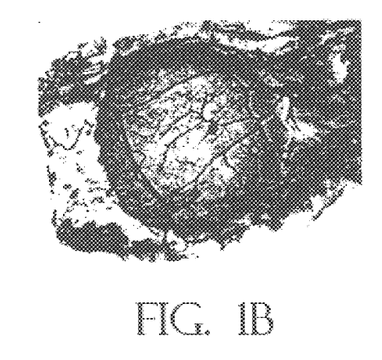
Figure 1C:
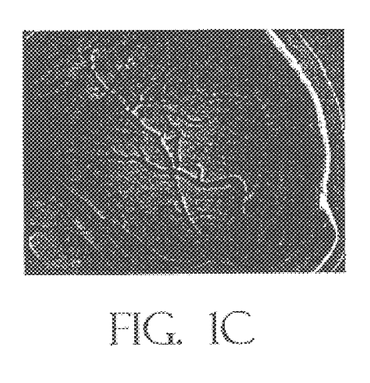
Figure 1D:
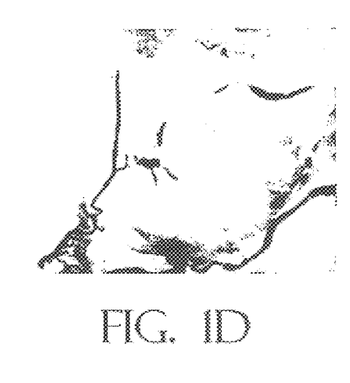

FIGS. 1A–1D show control eggs and test eggs in the aforementioned assay: FIG. 1A, saline control (no treatment); FIG. 1B, bFGF; FIG. 1C, bFGF plus GST; FIG. 1D, bFGF plus GST-SEQ ID NO:10. The substantial inhibition of bFGF-induced angiogenesis by GST-SEQ ID NO:10 is apparent in FIG. 1D.

Example 3
Inhibition of Endothelial Cell Migration to Vitronectin

Endothelial cells must migrate prior to penetrating the basement membrane. Migration of endothelial cells to vitronectin is a process closely related to angiogenesis.

The lower side of 8 $\mu$m pore transwell inserts (Costar, Inc.) were coated with 2 $\mu$g/ml of vitronectin for one hour and blocked with 2% bovine serum albumin in phosphate buffered saline for one hour. The inserts were then placed into 24 well culture dishes containing 500 $\mu$l migration buffer in the lower chamber. Twenty-five thousand HUVECs in 50 $\mu$l of migration buffer were added to the upper chamber of duplicate inserts containing 50 $\mu$l of a solution of 50 $\mu$g/ml GST-SEQ ID NO. 10 peptide in migration buffer (Herpes buffered M199 medium containing 1% BSA, 2 $\mu$M $MgCl_2$, 2 $\mu$M $CaCl_2$ and 0.2 $\mu$M $MnCl_2$) or migration buffer alone. Cells were allowed to migrate from the upper to the lower chamber for four hours at 37° C. Nonmigratory cells were removed from the upper surface by wiping the upper side with an absorbent tip. Cells which migrated to the lower side of the transwell insert were then fixed for 15 minutes with 3.7% paraformaldehyde in phosphate buffered saline and stained with a 2% crystal violet solution. After extensive water washing to remove excess crystal violet, the number of cells which had migrated were counted in three representative high power (200X) fields per inset.

Peptide GST-SEQ ID NO: 10 at a concentration of 0.27 $\mu$M achieved 100% inhibition of HUVEC migration to vitronectin.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A method of inhibiting endothelial cell proliferation comprising contacting endothelial cells with a compound of the formula $$X_1\text{-(SEQ ID NO:2)-}X_2 \qquad (I)$$

wherein $X_1$ is from zero to 25 amino acids; and $X_2$ is from zero to 60 amino acids, and wherein said compound optionally comprises an amino-terminal and optionally comprises a carboxy-terminal protecting group.

2. The method of claim 1 wherein $X_1$ is from zero to 12 amino acids, and $X_2$ is from zero to 45 amino acids.

3. The method of claim 1 wherein $X_1$ is
  (i) zero amino acids, or
  (ii) the segment SEQ ID NO:3, or N-terminal truncation fragment thereof containing at least one amino acid, and $X_2$ is
  (i) zero amino acids, or
  (ii) the segment SEQ ID NO:4, or C-terminal truncation fragment thereof containing at least one amino acid.

4. The method of claim 1 wherein the compound has the amino acid sequence SEQ ID NO:5.

5. The method of claim 1 wherein the compound has the amino acid sequence SEQ ID NO:6.

6. The method of claim 1 wherein the compound has the amino acid sequence SEQ ID NO:7.

7. The method of claim 1 wherein the compound has the amino acid sequence SEQ ID NO:9.

8. The method of claim 1 wherein the compound has the amino acid sequence SEQ ID NO:10.

9. A method of inhibiting endothelial cell proliferation comprising contacting endothelial cells with the compound SEQ ID NO:8, wherein said compound optionally comprises an amino-terminal and optionally comprising a carboxy-terminal protecting group.

10. A method of inhibiting endothelial cell proliferation comprising contacting endothelial cells with the compound SEQ ID NO:11, wherein said compound optionally comprises an amino-terminal and optionally comprising a carboxy-terminal protecting group.

11. A method of inhibiting endothelial cell proliferation comprising contacting endothelial cells with the compound SEQ ID NO:12, wherein said compound optionally comprises an amino-terminal and optionally comprising a carboxy-terminal protecting group.

12. A pharmaceutical composition comprising a pharmaceutically acceptable carrier and a compound of the formula $$X_1\text{-(SEQ ID NO:2)-}X_2 \qquad (I)$$

wherein $X_1$ is from zero to 25 amino acids; and $X_2$ is from zero to 45 amino acids, and wherein said compound optionally comprises an amino-terminal and optionally comprises a carboxy-terminal protecting group.

13. The composition of claim 12 wherein $X_1$ is from zero to 12 amino acids, and $X_2$ is from zero to 32 amino acids.

14. The composition of claim 12 wherein $X_1$ is
  (i) zero amino acids, or
  (ii) the segment SEQ ID NO:3, or N-terminal truncation fragment thereof containing at least one amino acid, and $X_2$ is
  (i) zero amino acids, or
  (ii) the segment SEQ ID NO:4, or C-terminal truncation fragment thereof containing at least one amino acid.

15. The composition of claim 12 wherein $X_1$ has a substantial amino acid homology to SEQ ID NO:3 and $X_2$ has a substantial amino acid homology to SEQ ID NO:4.

16. The composition of claim 12 wherein the compound has the amino acid sequence SEQ ID NO:5.

17. The composition of claim 12 wherein the compound has the amino acid sequence SEQ ID NO:6.

18. The composition of claim 12 wherein the compound has the amino acid sequence SEQ ID NO:7.

19. The composition of claim 12 wherein the compound has the amino acid sequence SEQ ID NO:9.

20. The composition of claim 12 wherein the compound has the amino acid sequence SEQ ID NO:10.

21. A pharmaceutical composition comprising a pharmaceutically acceptable carrier and the compound SEQ ID NO:8, wherein said compound optionally comprises an amino-terminal and optionally comprises a carboxy-terminal protecting group.

22. A pharmaceutical composition comprising a pharmaceutically acceptable carrier and the compound SEQ ID NO:11, wherein said compound optionally comprises an amino-terminal and optionally comprises a carboxy-terminal protecting group.

23. A pharmaceutical composition comprising a pharmaceutically acceptable carrier and the compound SEQ ID NO:12, wherein said compound optionally comprises an amino-terminal and optionally comprises a carboxy-terminal protecting group.

24. A method of inhibiting angiogenesis comprising administering to a mammal an effective amount of a composition according to any one of claims 12, 21, 22, or 23.

25. A method of inhibiting endothelial cell proliferation comprising administering to a mammal an effective amount of a composition according to any one of claims 12, 21, 22, or 23.

* * * * *

UNITED STATES PATENT AND TRADEMARK OFFICE
CERTIFICATE OF CORRECTION

| | | |
|---|---|---|
| PATENT NO. | : 6,284,726 B1 | Page 1 of 1 |
| APPLICATION NO. | : 09/612126 | |
| DATED | : September 4, 2001 | |
| INVENTOR(S) | : Robert W. Colman and Shaker A. Mousa | |

It is certified that error appears in the above-identified patent and that said Letters Patent is hereby corrected as shown below:

Column 1, before line 5, insert:

--REFERENCE TO GOVERNMENT GRANT

This invention was made with government support under grant P01 HL56914 awarded by the National Institutes of Health. The government has certain rights in the invention.--

Signed and Sealed this

Eleventh Day of October, 2011

David J. Kappos
*Director of the United States Patent and Trademark Office*